United States Patent [19]
Kenneally et al.

[11] Patent Number: 6,121,440
[45] Date of Patent: Sep. 19, 2000

[54] PROCESS FOR SYNTHESIS OF POLYOL FATTY ACID POLYESTERS

[75] Inventors: Corey James Kenneally, Maineville; Gary Allen Busch, Cincinnati; Patrick Joseph Corrigan, Cincinnati; Eric Paul Granberg, Cincinnati; John Keeney Howie, Oregonia; Richard Gerard Schafermeyer, Cincinnati; James Earl Trout, West Chester, all of Ohio

[73] Assignee: The Procter & Gamble Company, Cincinnati, Ohio

[21] Appl. No.: 09/022,751

[22] Filed: Feb. 12, 1998

Related U.S. Application Data

[60] Provisional application No. 60/073,029, Jan. 29, 1998.

[51] Int. Cl.$^7$ .............................. C07C 51/00; C11C 1/00; C11C 3/00
[52] U.S. Cl. ......................... 536/115; 536/119; 536/124; 554/168; 554/171; 554/172
[58] Field of Search ..................... 554/167, 168, 554/170, 171, 172; 536/115, 119, 124

[56] References Cited

U.S. PATENT DOCUMENTS

| | | |
|---|---|---|
| 2,893,990 | 7/1959 | Hass et al. . |
| 3,251,827 | 5/1966 | Schnell et al. . |
| 3,558,597 | 1/1971 | von Brachel et al. . |
| 3,644,333 | 2/1972 | Osipow et al. . |
| 3,792,041 | 2/1974 | Yamagishi et al. . |
| 3,963,699 | 6/1976 | Rizzi et al. . |
| 4,032,702 | 6/1977 | James ........................................ 536/119 |
| 4,298,730 | 11/1981 | Galleymore et al. .................... 536/119 |
| 4,334,061 | 6/1982 | Bossier et al. .......................... 536/119 |
| 4,517,360 | 5/1985 | Volpenhein .............................. 536/119 |
| 4,518,772 | 5/1985 | Volpenhein .............................. 536/119 |
| 4,877,871 | 10/1989 | Klemann et al. ....................... 536/124 |
| 4,973,682 | 11/1990 | Willemse ................................. 536/119 |
| 5,231,199 | 7/1993 | Willemse ................................. 554/174 |
| 5,648,483 | 7/1997 | Granberg et al. ....................... 536/119 |

FOREIGN PATENT DOCUMENTS

| | | | |
|---|---|---|---|
| 92/04361 | 3/1992 | WIPO | .......................................... 13/6 |

OTHER PUBLICATIONS

U.S. application No. 08/683,899, Corrigan et al., filed Jul. 19, 1996.

U.S. application No. 08/976,459, Corrigan et al., filed Oct. 21, 1997.

*Primary Examiner*—Nathan M. Nutter
*Attorney, Agent, or Firm*—James F. McBride; Karen F. Clark; Jacobus C. Rasser

[57] ABSTRACT

A process for preparing esterified polyol fatty acid polyesters is provided, where the polyol has n hydroxyl groups. The process provides for independent control of the level of fully esterified polyols, on the one hand, and the level of n−3 and lower esters, on the other hand. The process is especially suited for preparing sucrose polyester, wherein the process provides for independent control of the level of octaesters, on the one hand, and penta and lower level esters, on the other hand. The process can be used to reduce the level of undesirable reaction byproducts, such as difatty ketone and beta ketoester.

30 Claims, No Drawings

PROCESS FOR SYNTHESIS OF POLYOL FATTY ACID POLYESTERS

This application claims priority to Provisional Application Ser. No. 60/073,029 filed on Jan. 29, 1998.

TECHNICAL FIELD

This invention relates to improved synthesis of higher polyol fatty acid polyesters, especially sucrose polyesters, and more particularly to a process that is capable of making said polyesters more efficiently and/or making said polyesters of improved quality.

BACKGROUND OF THE INVENTION

Processes for preparing polyol fatty acid polyesters, including processes that utilize solvent-free transesterification reactions, have been described in U.S. Pat. No. : 3,963,699, Rizzi et al., issued Jun. 15, 1976; U.S. Pat. No. 4,517,360, Volpenhein, issued May 14, 1985; and U.S. Pat. No. 4,518,772, Volpenhein, issued May 21, 1985. Additional patents describing processes for preparing lower and higher esters of polyols include U.S. Pat. No. : 2,893,990, Hass et al., issued Jul. 7, 1959; U.S. Pat. No. 3,251,827, Schnell et al., issued May 17, 1966, which discloses that the particle size of the sugar should be kept small to avoid formation of higher esters; U.S. Pat. No. 3,558,597, Brachel et al., issued Jan. 26, 1971; U.S. Pat. No. 3,644,333, Osipow et al., issued Feb. 22, 1972; U.S. Pat. No. 3,792,041, Yamagishi et al., issued Feb. 12, 1974, which discloses making a solution of sucrose and fatty acid soap in water and adding the fatty acid ester and catalyst before elevating the temperature to drive off the water; U.S. Pat. No. 4,032,702, James, issued Jun. 28, 1977, which discloses using lower esters of sucrose as emulsifiers in the preparation of lower esters and the use of soap as a catalyst for such reactions; U.S. Pat. No. 4,298, 730, Galleymore et al., issued Nov. 3, 1981, which also discloses the use of soap as an emulsifier and catalyst; U.S. Pat. No. 4,334,061, Bossier et al., issued Jun. 8, 1982, which discloses the use of a water washing step to purify the polyol polyester and incidentally discloses the use of inert gas sparging to remove lower alcohol from the reaction between sucrose and lower alkyl ester of fatty acid to speed the reaction and the removal of unreacted sucrose from an initial stage of a batch reaction for no indicated reason; and U.S. Pat. No. 4,877,871, Klemann et al., issued Oct. 31, 1989. PCT publication WO 92/04361 published Mar. 19, 1992 discloses a process for obtaining highly esterified polyol fatty acid polyesters having reduced levels of difatty ketones and beta-ketoesters, which publication is incorporated herein by reference.

It can be desirable to reduce the level of partially esterified polyol in a reaction product comprising polyol polyesters. Typically, the level of partially esterified polyol esters are reduced by reacting the higher level polyol polyesters to even higher levels. For instance, in the case of sucrose fatty acid polyesters, the level of hexa, penta, and other lower esters is typically reduced by increasing the level of sucrose octaester. This has the disadvantage that higher levels of sucrose octaester are typically associated with high levels of other byproducts, such as difatty ketones and beta-ketoesters. In addition, higher level of octaester production typically result in higher production costs.

SUMMARY OF THE INVENTION

The present invention relates to improved, preferably continuous, processes for preparing esterified polyol fatty acid polyester. The present invention provides a process whereby the level of partially esterified polyol is decoupled from the level of more fully esterified polyol. For a polyol having n esterifiable hydroxy groups, the present invention provides a process for decoupling the level of n-y and lower esterified polyols from the level of n esterified polyol (fully esterified), where n-y and lower esterified polyols are considered to be at least partially digestible within the human gastrointestinal tract.

In one embodiment, the present invention provides a process whereby the level of n-3 and lower esterified polyol is decoupled from the level of n esterified polyol. In particular, in the case of sucrose (n=8), the present invention provides for independent control of the level of sucrose hexa (n=2), penta (n=3), and other lower esters, on the one hand, and the level of sucrose octaesters on the other hand. Accordingly, a desired, relatively low level of hexa, penta and lower esters can be achieved, while maintaining a moderate level of octaester.

A process according to one embodiment of the present invention comprises a continuous, solvent free process for preparing polyol fatty acid polyesters by interesterifying polyol containing more than about four esterifiable hydroxy groups and fatty acid ester. The process comprises:

1) a first stage reaction providing a first stage reaction product having a level of unreacted polyol of less than about 0.50 percent, and wherein the degree of esterification of the reacted polyol in the first stage reaction product is between about 15 percent and about 75 percent; and 2) a second stage reaction, the second stage reaction receiving the first stage reaction product and providing further esterification of the first stage reaction product to provide a second stage reaction product, wherein the second stage reaction is controlled to maintain a degree of esterification of the polyol such that no more than about 85 percent, and preferably between about 70 percent and about 85 percent by weight of the esterified polyol molecules in the second stage reaction product are fully esterified.

According to the present invention, for a polyol molecule having n hydroxyl groups available for esterification, the second stage reaction is controlled to reduce the level of n−3 and lower level polyol esters to less than about 1.5 percent, more preferably less than about 1.0 percent and still more preferably less than about 0.50 percent by weight of the esterified polyol molecules, while maintaining between about 70 percent and about 85 percent by weight of the esterified polyol molecules fully esterified. In one embodiment, the level of penta and lower level polyol esters is reduced to less than about 0.50 percent by weight of the esterified polyol molecules while reducing the level of fully esterified polyol molecules.

The relative distribution of individual esters (e.g. octa, hepta, hexa, penta) is determined in accordance with the method "Ester Distribution of Sucrose Polyesters" described in PCT publication WO 94/09637, "Nondigestible Fat Compositions Containing Solid Polyol Polyester Polymer for Passive Oil Loss Control," published May 11, 1994 in the name of Corrigan et al. and claiming priority to U.S. patent application Ser. No. 07/968,791 filed Oct. 30, 1992; as well as in "Measurement of the Relative Ester Distribution of Olestra Test Material" dated Dec. 19, 1995 (available from the Office of Premarket Approval, Center for Food Safety and Applied Nutrition (HFS-200), Food and Drug Admin., 200 C St. SW., Washington, D.C.); and as set forth in the Food Chemicals Codex, $1^{st}$ Supplement to the $4^{th}$ Edition, National Academy Press, 1997; which publications and patent application are incorporated herein by reference.

The second stage reaction can be controlled by one, or a combination of one or more, of the following methods: by reducing the level of unreacted polyol in the first stage reaction product to less than about 0.50 percent; by controlling the residence time of the polyol esters in the second stage reaction; by controlling the level of lower alkyl (C1–C4) alcohol in the second stage reaction; and by heating the reaction products of the second stage reaction in the absence of C1–C4 lower alcohol removing methods.

In one embodiment, the process comprises controlling the level of C1–C4 alcohol in the second stage reaction by providing a sufficient level of C1–C4 alcohol to maintain the level of fully esterified polyol to between about 70 percent and about 85 percent of the esterified polyol molecules, while reducing the level of n-3 and lower esters. The step of providing a sufficient level of C1–C4 alcohol can comprise adding methanol to the second stage reaction or by providing a recycled inert gas sparge containing methanol.

According to one embodiment of the present invention, the process comprises providing a reaction product of sucrose fatty acid polyester comprising no more than about 85 percent, preferably between about 70 and about 85 percent by weight sucrose octaester and no more than about 1.0 percent by weight penta and lower sucrose esters, and reducing the level of penta and lower sucrose ester to less than about 0.6 percent by weight while maintaining the level of sucrose octaester between about 70 and about 85 percent. The step of reducing the level of penta and lower sucrose ester can comprise reducing the level of penta and lower sucrose ester without increasing the level of sucrose octaester.

DETAILED DESCRIPTION OF THE INVENTION

The Polyol

As used herein, the term "polyol" is intended to include any linear, cyclic, or aromatic compound containing at least four free esterifiable hydroxyl groups. In practicing the process disclosed herein, sucrose is the most highly preferred polyol. If sucrose is not used, then the selection of a suitable alternative polyol is simply a matter of choice. For example, suitable polyols can be selected from the following classes: saturated and unsaturated straight and branched chain linear aliphatics; saturated and unsaturated cyclic aliphatics, including heterocyclic aliphatics; or mononuclear or polynuclear aromatics, including heterocyclic aromatics. Carbohydrates and nontoxic glycols are preferred polyols. Monosaccharides suitable for use herein include, for example, mannose, galactose, arabinose, xylose, ribose, fructose, sorbose, and erythrulose. Oligosaccharides suitable for use herein include, for example, maltose, cellobiose, lactose, trehalose, sucrose and raffinose. Polysaccharides suitable for use herein include, for example, amylose, glycogen, cellulose, chitin, inulin, agarose, zylans, mannan and galactans. Although sugar alcohols are not carbohydrates in a strict sense, the naturally occurring sugar alcohols are so closely related to the carbohydrates that they are also preferred for use herein. The sugar alcohols most widely distributed in nature and suitable for use herein are sorbitol, mannitol and galactitol. It is desirable that the aldehyde groups in the polyol be changed to alcohol groups or reacted with alcohol groups to form acetal linkages, such as sorbitol or sorbitan. Alkoxylated polyols such as ethoxylated glycerin, ethoxylated polyglycerol, ethoxylated sorbitol, or ethoxylated sorbitan can also be used. Polyglycerol is also a suitable polyol for use herein.

Particularly preferred classes of materials suitable for use herein include the monosaccharides, the disaccharides and sugar alcohols. Preferred carbohydrates and sugar alcohols include xylitol, sorbitol, and sucrose. The most preferred is sucrose.

Fatty Acid Ester of Easily Removable Alcohol

As used herein, the terms "fatty acid ester(s)" and "ester reactant(s)" are intended to include any compound wherein the alcohol portion is easily removed, including polyols and substituted alcohols, etc., but are preferably esters of volatile alcohols, e.g., the $C_1$–$C_4$ alcohols (preferably methyl), 2-methoxy ethyl and benzyl esters of fatty acids containing about eight or more carbon atoms, and mixtures of such esters. Volatile alcohols are highly desirable. Methyl esters are the most highly preferred ester reactants. Suitable ester reactants can be prepared by the reaction of diazoalkanes and fatty acids, or derived by alcoholysis from the fatty acids naturally occurring in fats and oils. Suitable fatty acid esters can be derived from either synthetic or natural, saturated or unsaturated fatty acids and include positional and geometrical isomers. Suitable preferred saturated fatty acids include caprylic, capric, lauric, myristic, palmitic, stearic, arachidic, behenic, isomyristic, isomargaric, myristic, caprylic, and anteisoarachadic. Suitable preferred unsaturated fatty acids include myristoleic, palmitoleic, ricinoleic, linoleic, oleic, elaidic, linolenic, eleasteric, arachidonic, erucic, and erythrogenic acids. Mixtures of fatty acids derived from soybean oil, cottonseed oil, palm oil, safflower oil, rapeseed oil, canola (low erucic acid), and corn oil are especially preferred for use herein. The fatty acids can be used "as is," and/or after hydrogenation, and/or isomerization, and/or purification. For example, rapeseed provides a good source for $C_{22}$ fatty acid; $C_{16}$–$C_{18}$ fatty acid can be provided by tallow, soybean oil, or cottonseed oil; and shorter chain fatty acids can be provided by coconut, palm kernel, or babassu oils. Lard, olive oil, peanut oil, sesame seed oil, and sunflower seed oil, are other natural sources of fatty acids.

Some useful solid polyol fatty acid polyesters are those wherein the ester groups comprise a combination of: (i) long chain, unsaturated fatty acid radicals and/or short chain saturated fatty acid radicals, and (ii) long chain saturated fatty acid radicals, the ratio of (i):(ii) being from about 1:15 to about 2:1, and wherein at least about 15% (preferably at least about 30%, more preferably at least about 50%, and most preferably at least about 60%) by weight of the total fatty acid radicals in the solid polyol polyester are $C_{20}$ or higher saturated fatty acid radicals. The long chain unsaturated fatty acid radicals are typically, but not necessarily, straight chain (i.e., normal) and contain at least about 12 (preferably about 12 to about 26, more preferably about 18 to 22) carbon atoms. The most preferred unsaturated radicals are the $C_{18}$ mono and/or diunsaturated fatty acid radicals. The short chain saturated fatty acid radicals are typically, but not necessarily, normal and contain 2 to 12 (preferably 6 to 12 and most preferably 8 to 12) carbon atoms. More preferred long chain saturated fatty acid radicals are typically, but not necessarily, normal and contain at least 20 (preferably 20 to 26, most preferably 22) carbon atoms. The molar ratio of Group (i) fatty acid radicals to Group (ii) fatty acid radicals in the polyester molecule is from about 1:15 to about 2:1 (preferably from about 1:7 to about 5:3, more preferably from about 1:7 to about 3:5). A typical suitable range is about 3:5 to 4:4. The average degree of esterification of these solid polyol fatty acid polyesters is such that at least 4 of the hydroxyl groups of the polyol are esterified. In the case of sucrose polyesters, from about 7 to 8 of the hydroxyl groups of the polyol are preferably esterified.

Some especially useful solid polyol polyesters prepared by the processes herein contain a combination of: (i) long chain (at least 12 carbon atoms) unsaturated fatty acid radicals, or a mixture of said radicals and saturated short chain ($C_2$–$C_{12}$) fatty acid radicals, and (ii) long chain (at least 20 carbon atoms) saturated fatty acid radicals, in a molar ratio of (i) to (ii) of from about 1:15 to about 2:1, and wherein at least four of the hydroxyl groups of the polyol are esterified.

Examples of long chain unsaturated and polyunsaturated fatty acid radicals for the solid polyol polyesters herein are lauroleate, myristoleate, palmitoleate, oleate, elaidate, erucate, linoleate, linolenate, arachidonate, eicosapentaenoate, and docosahexaenoate. For oxidative stability, the mono- and diunsaturated fatty acid radicals are preferred.

Examples of suitable short chain saturated fatty acid radicals are acetate, butyrate, (caproate), hexanoate (caprylate), decanoate (caprate) and dodecanoate (laurate). Use of more volatile ester reactants may require modification of the process, e.g., use of reflux in the reactors or other means to prevent excessive loss of said reactants.

Examples of suitable long chain saturated fatty acid radicals are eicosanoate (arachidate), docosanoate (behenate), tetracosanoate (lignocerate), and hexacosanoate (cerotate).

Of course, the long chain unsaturated fatty acid radicals can be used singly or in mixtures with each other or in mixtures with the short chain saturated fatty acid radicals, in all proportions. Likewise, the long chain saturated acid radicals can be used in combination with each other in all proportions. Mixed fatty acid radicals from source oils which contain substantial amounts of the desired unsaturated or saturated acids can be used as the fatty acid radicals to prepare compounds of the invention. The mixed fatty acids from the oils should contain at least about 30% (preferably at least about 50%, and most preferably at least about 80%) of the desired unsaturated or saturated acids. For example, rapeseed oil fatty acids or soybean oil fatty acids can be used instead of pure $C_{12}$–$C_{26}$ unsaturated fatty acids. Hardened (i.e., hydrogenated) high erucic rapeseed oil fatty acids can be used instead of pure $C_{20-26}$ saturated acids. Preferably the $C_{20}$ and higher acids (or their derivatives, e.g., methyl esters) are concentrated, for example by distillation. The fatty acids from palm kernel oil or coconut oil can be used as a source of $C_8$ to $C_{12}$ acids.

The preferred long chain saturated fatty acid radical is behenate. Preferred solid polyol polyesters of the invention are polyesters of sucrose in which at least 7 of the 8 hydroxyl groups are esterified.

Examples of such solid polyol polyesters are sorbitol hexaester in which the acid ester radicals are palmitoleate and arachidate in a 1:2 molar ratio; the octaester of raffinose in which the acid ester radicals are linoleate and behenate in a 1:3 molar ratio; the heptaester of maltose wherein the esterifying acid radicals are sunflower seed oil fatty acids and lignocerate in a 3:4 molar ratio; the octaester of sucrose wherein the esterifying acid radicals are oleate and behenate in a 2:6 molar ratio; and the octaester of sucrose wherein the esterifying acid radicals are laurate, linoleate and behenate in a 1:3:4 molar ratio. A preferred material is sucrose polyester in which the degree of esterification is 7–8, and in which the fatty acid radicals are $C_{18}$ mono- and/or diunsaturated and behenic, in a molar ratio of unsaturates:behenic of from about 1:7 to about 3:5.

Solid polyol polyesters preferably have complete melting points above about 25° C. (77 ° F.), more preferably above about 37° C. (98.6° F.), even more preferably above about 50° C. (122 ° F.) and most preferably above about 60° C. (140 ° F.). Melting points reported herein are measured by Differential Scanning Calorimetry (DSC). These solid materials have the ability to trap relatively large amounts of oil within their crystal structure. As a consequence, they can be used as "hardstocks" by blending them in amounts of from about 1% to about 50% (typically from about 1% to about 25%) with liquid oils, to prepare semi-solid compositions. A typical suitable range is from about 10% to about 25%. The oils for these compositions can be conventional digestible triglyceride oils such as cottonseed, corn, canola, or soybean oil, or nondigestible edible oils.

As disclosed herein before, other suitable polyol polyesters that can be prepared by the processes herein include the polyol polyesters disclosed in the patents incorporated herein by reference, especially U.S. Pat. Nos.: 3,963,699; 4,517,360; and 4,518,772.

The fatty acid composition (FAC) of the polyol polyesters can be determined by gas chromatography, using a Hewlett-Packard Model 5712A gas chromatograph equipped with a thermal conductivity detector and a Hewlett-Packard Mode 17671A automatic sampler. The chromatographic method used is described in *Official Methods and Recommended Practices of the American Oil Chemists Society*, 3rd Ed., 1984, Procedures 1-$C_e$62 (incorporated herein by reference).

It is very important for the preparation of improved polyol polyesters that the fatty acid esters be highly purified to remove color/odor materials, oxidation products, and/or their precursors. Such materials include those that have a color, odor, or taste that is objectionable, or which develop an objectionable color, odor, or taste upon heat treatment and/or oxidation. In addition, highly polar materials which coat the catalyst surface should be removed. Preferably, the carbonyl value should be less than about 200 ppm, more preferably less than about 100 ppm, and even more preferably less than about 50 ppm. Processes for preparing such fatty acid esters are disclosed in U.S. Pat. No. 4,931,552, Gibson et al., issued Jun. 5, 1990, said patent being incorporated herein by reference. The percent transmittance at 375 nm with a heptane standard should be greater than zero, preferably greater than about 60, most preferably greater than about 80. For typical ester sources without added colored materials, these values define operable reactants. I.e., the carbonyl content is generally indicative of the total level of polar materials present. The low level of color/odor materials and/or oxidation products in the reactants helps provide improved color polyol polyester products that can be further improved by a combination of the process improvements set forth herein.

Removal of Unreacted Polyol and/or Large Particle Catalyst at an Early Stage of the Reaction Unreacted polyol and/or large particle catalyst are desirably removed at an early stage of the reaction, e.g., before the polyol is esterified to more than about 75% and, preferably, (a) after the degree of interesterification is greater than about 15%, preferably greater than about 40%, and (b) while any soap that is present is still soluble in the reaction mixture. Removal at an early stage is more convenient than in a later stage due to the low viscosity of the reaction mixture and minimizes production of unwanted by-products. Unreacted polyol, such as sucrose, can interfere with the orderly progress of the reaction in the later stages where it limits the desired interesterification reaction by degrading, and/or preferentially reacting with the active form of the catalyst and/or by continuing to create undesirable by-products such as color bodies.

In a preferred embodiment the soap and polyol can be co-milled in a suitable mill such as a jet mill, hammer mill or air swept mill.

Removal of unreacted polyol and/or large size catalyst can be accomplished by, e.g., filtration and/or by centrifugation if the polyol is a solid in the reaction mixture. The resulting reaction mixture that is free of unreacted polyol will then react faster and reach the desired degree of esterification quicker than if the polyol remains. The key to the improved reaction kinetics is to lower the level of unreacted polyol to less than about 0.5%, and preferably less than about 0.20% and most preferably the reaction is substantially free of any unreacted polyol, i.e., less than 0.02%. The filtered polyol and/or any catalyst removed with it can be returned to an earlier stage of the reaction or discarded.

One way to keep the unreacted polyol level below about 0.5% is to control the reaction conditions in the first stage so that less than 0.5% unreacted polyol remains, and more preferably below about 0.20%.

Catalyst

The basic catalysts generally suitable for use in preparing the polyol polyesters are those selected from the group consisting of alkali metals, such as sodium, lithium and potassium: alloys of two or more alkali metals, such as sodium-lithium and sodium-potassium alloys; alkali metal hydrides, such as sodium, lithium and potassium hydride; and alkali metal alkoxides, such as potassium t-butoxide, potassium methoxide, and/or sodium methoxide. Potassium methoxide is preferred, especially when used with potassium soap.

In another particularly preferred embodiment of the present invention, the basic catalyst used in the reaction is potassium carbonate, sodium carbonate, barium carbonate, or mixtures of these compounds having particle sizes that are less than about 100 microns, preferably less than about 50 microns. It has been found that when these specific compounds are used as catalysts, increased yields of light colored higher polyol polyesters are obtained when compared to essentially identical reactions carried out using more conventional catalysts, such as sodium hydroxide, potassium hydride, soap, or sodium methoxide. These preferred catalysts can also be used in admixture with the more conventional basic catalysts, described above. Potassium carbonate and/or potassium methoxide are the most preferred catalysts for use herein. The use of these catalysts is further disclosed and claimed in U.S. Pat. No. 4,517,360, Volpenhein, issued May 14, 1985, said patent being incorporated herein by reference.

More reactive catalysts such as potassium or sodium methoxide should be protected until their addition into the reaction mixture. Preferably the catalyst should be suspended in or more preferably encapsulated by a material that will either be present in the reaction mixture or be readily separated from the reaction mixture. Suitable encapsulating agents include said alkyl esters of, e.g., $C_{16}$–$C_{22}$ fatty acids.

The level of catalyst is kept as low as possible, as discussed more fully hereinafter, typically from about 0.01 to about 0.5 moles of catalyst per mole of polyol. The level of catalyst can be lowered to the least amount that is effective to give a reasonable rate of reaction. It is possible to have very fast reactions using only the residual base in, e.g., the soap emulsifier commonly used in such reactions. It is desirable to keep the level of base as low as possible to minimize formation of color and/or odor bodies and/or excess soap and/or by-products. It is also desirable to effect the removal of oversize catalyst after the first phase of the reaction, and/or the destruction and removal of the catalyst after the reaction has reached the desired end point.

Small Particle Size Polyol Obtained by Mechanical Size Reduction

The use of small particle size polyol, e.g., sucrose, in esterification reactions to form polyol polyesters is highly desirable to improve the speed of reaction. In reactions that use a solvent to form a homogeneous reaction mixture, there is little need for the small particle size, since the polyol is dissolved by the solvent. However, in solventless, heterogeneous reactions of the type herein, small particle size is highly desirable because smaller particles have a larger surface that are exposed to the liquid which greatly improves the reaction kinetics. The small particle size can also be achieved by art-disclosed methods in which the polyol, e.g., sucrose, is dissolved in water and then the water is removed after the other reactant ingredients and/or catalyst are present to form small particles of the polyol in situ. There is no general consensus, or appreciation, in such art that the primary factor that improves the reaction is the resulting small particle size of the polyol. Furthermore, although this preliminary step of dissolving the polyol in water provides the desired small particle size, it requires the removal of water from the reaction mixture, usually at a time when other ingredients are present, and the presence of water can promote the formation of undesirable side products. It is especially undesirable in a continuous process.

An improved reaction can be achieved without the use of solvent, either in a preliminary step, or in the reaction itself, if the particle size of the solid polyol is less than about 100 microns, preferably less than about 50 microns, more preferably less than about 10 microns. These particle sizes can be achieved, e.g., by a combination of grinding, milling, and/or sieving. It is surprising that the particles of these sizes, prepared by simple mechanical size reduction methods, provide the benefits of the prior art processes requiring water solutions that give particle diameters below one micron.

Emulsifier

Emulsifiers help to solubilize the polyol in the methyl fatty acid esters. Polyol fatty acid esters having less than 4 hydroxy groups esterified with fatty acids are useful emulsifiers. Highly preferred emulsifiers are sucrose mono esters, diesters and triesters of $C_{12}$–$C_{20}$ fatty acids. It is preferred that the lower polyol fatty acid esters be the same as the polyol polyester being synthesized to avoid separation problems at the completion of the reaction.

These lower polyol esters are preferred emulsifiers. One way to obtain them is by generation in the reaction itself. This is accomplished by reacting the polyol with fatty acids under conditions that encourages formation of lower esters initially and then adding more fatty acids later. Alkali metal soaps can also be used as emulsifiers in the processes described herein. As used herein, the term "alkali metal fatty acid soap" is intended to include the alkali metal salts of saturated and unsaturated fatty acids having from about 8 to about 18 carbon atoms. Suitable alkali metal fatty acid soaps include, for example, lithium, sodium, potassium, rubidium, and cesium salts of the fatty acids described above. Mixtures of fatty acids derived from soybean oil, sunflower oil, safflower oil, and corn oil are preferred for use herein. Preferred alkali metal fatty acid soaps include potassium soap made from soybean oil, preferably hydrogenated soybean oil.

The level of soap should be at least enough to dissolve the polyol at an acceptable rate. The level of soap can be reduced as a result of using smaller particle polyol, e.g., sucrose, and/or reaction conditions that favor the solubilization of the polyol. Excessive soap can cause foaming and undesirable thickening. The level of soap in the first stage of the reaction is usually from about 0.001 to about 0.6, preferably from about 0.05 to about 0.1 moles of soap per mole of polyol. The soap is preferably used in combination with another emulsifier, preferably with the lower esters of the polyol and the fatty acid which are present either by being added as part of the initial reaction mixture, or by backmixing. The desire is to have little or no soap in the second stage as it increases the viscosity of the reaction and inhibits alcohol transfer from the reaction mixture. This will increase the rate of the reaction.

After the average degree of esterification reaches about 60%, the soap is no longer needed to facilitate the reaction and, therefore, can be removed. Soap emulsifier is not essential after the polyol has reacted once and there is sufficient lower ester to maintain the homogeniety of the reaction mixture.

Removal of soap can be accomplished, e.g., by filtration, centrifugation, etc., since the soap is relatively insoluble in the reaction mixture at such higher degrees of esterification. The resulting filtered reaction mixture does not need to be recatalyzed, and, the reaction proceeds at a much higher rate than if the soap were present. The filtered reaction mixture typically has a soap level of less than about 0.5, preferably less than about 0.1 moles of soap per mole of polyol, more preferably less than about 0.05 moles of soap per mole of polyol. The filtered material can be returned to the initial stage of the reaction, if desired.

Back Mixing

It is highly desirable to conduct the initial stage, or stages, of the reaction under back-mixing conditions to maintain the degree of esterification between about 15% and about 75%, preferably between about 35% and about 55%. This degree of esterification provides sufficient lower partial polyol polyester to aid in the solubilization of the poorly soluble polyol and to provide a stable heterogeneous reaction mixture that minimizes unreacted polyol, and the distribution/composition and/or level of lower esters and/or soap that cause foaming is low enough to permit continuous reaction without overfoaming. Levels of conversion below about 20% can require low levels of soap, higher pressure or vigorous agitation to avoid overfoaming. In a continuous reaction, the individual reactants can be added to the first stage at a rate that maintains the desired degree of esterification and yet provides sufficient yield from the first stage to maintain the reaction in the subsequent stage, or stages.

It is desirable in the initial stage, or stages, of the process, and especially of a continuous process, to have a relatively high degree of completion. While the preferred degree of esterification is at least about 35%, more preferably at least about 45%, to minimize the amount of esterification that must take place in the final stages, removal of essentially all of the unreacted sucrose before entering the final stages greatly facilitates the reaction. Preferably, the final stages are carried out under conditions of plug flow. In the final stages, the reaction conditions are more stringent (lower pressure or higher sparge rates, or longer residence time etc.) and therefore more costly. Decreasing the time of the later stages and/or the size of the reactor is therefore generally desirable. Maintenance of the appropriate composition for solubilizing the polyol in the first stage is assisted by withholding a portion of the ester reactant from this initial stage, as described in U.S. Pat. No. 3,963,699, supra, incorporated herein by reference. In the initial stage, it is preferable to use only about 10% to about 50% of the total ester reactant, with the remainder being added in the later stages, especially where there are plug flow conditions.

Backmixing can be achieved in a continuous reaction, for example, by continually recycling a portion of the first stage reaction stream and/or by carrying out the reaction in a well agitated vessel (or, e.g., two vessels in series, or any other similar configuration that has hydrodynamically similar mixing conditions) where the reactants are continually added and the product is removed at rates that maintain the desired level of esterification. Although it is possible to start with plug flow conditions, the initial solubility of sucrose is low at the start of the reaction; the risk of unacceptable levels of foam when the degree of esterification is less than about 20% is great; and the resulting instability of the reaction mixture gives variable, poorly controlled esterification of the polyol. Without filtration of the unreacted reactants as discussed herein before, the conversion of the polyol can be poor and therefore plug flow is undesirable in the initial stages, especially without recycling.

If residual sucrose is detected in the first stage product, the product of the first stage is preferably filtered, or otherwise treated to remove substantially all of the unreacted polyol less than 0.5% should remain, and the unreacted solids are returned to the first stage, or, preferably, if at a lower level, discarded, since the ingredients are present, at least initially, at varying and unknown levels. If the reaction contains only low levels of soap emulsifier and catalyst, as preferred herein, the amount of material to be separated is minimal. Once steady state is achieved in a continuous reaction, the separated material can be cleaned up, e.g., by a purge stream, and recycled.

Backmixing in a batch process, can be approximated by using part of a previous batch that has the right degree of esterification, and adding reactants to the batch while the reaction is continuing until the appropriate degree of completion is reached, whereupon the addition of reactants is stopped and the reaction is taken to completion. A "semi-batch" reaction can be run by continually bringing batches to the appropriate intermediate degree of completion and then transferring at least the major portion of the batch to another vessel where the reaction is taken to completion.

Apparatus that is suitable for backmixing, and/or plug flow conditions, as discussed hereinafter, is disclosed in U.S. Pat. No. : 3,567,396, Setzler, issued Mar. 2, 1971; U.S. Pat. No. 3,679,368, Balint, et al., issued Jul. 25, 1972; U.S. Pat. No. 4,449,828, Mansour, issued May 22, 1984; U.S. Pat. No. 4,472,061, Mansour, issued Sep. 18, 1984; U.S. Pat. No. 4,543,194, Spence et al., issued Sep. 24, 1985; and U.S. Pat. No. 4,615,870, Armstrong et al., issued Oct. 7, 1986, all of said patents being incorporated herein by reference. Other disclosures of suitable processes and apparatus can be found in: The Degree of Mixing in Continuous Flow Systems, Zwietering, Chemical Engineering Science, pp. 1–15, Vol. 11, No. 1 (1959); Continuous Flow Stirred-Tank Reactor Systems, MacDonald and Piret, Chemical Engineering Progress, Vol. 47, No. 7, pp. 363–8 (July 1951); and Reaction Kinetics in a Tubular Reactor, Baron, Manning and Johnstone, Chemical Engineering Progress, Vol. 48, No. 3, pp. 125–132 (March 1952), all of said articles being incorporated herein by reference.

Use of Plug-Flow and/or Batch Conditions in the Final Stages to Increase Esterification The final stage, or stages, of the reaction should be carried out under plug-flow, or batch, conditions to prevent backmixing and thereby increase esterification. This plug flow can be approximated by feeding the output of the initial stage into a series of at least two continuous stirred tank reactors, but preferably is accomplished more efficiently in a continuous reactor, for example, in a tubular reactor and/or packed column and/or tray reactor and/or falling or rising film reactor, using more nearly plug-flow reactor apparatus. As discussed above, the plug flow conditions should be used after the degree of esterification of said polyol has reached at least about 35 to about 45%. The final sucrose octaester level should be between about 70 and about 85 weight percent of the esterfied sucrose.

In one embodiment, the tubular reactor and/or packed column and/or tray reactor and/or falling or rising film reactor will have the lower alkyl alcohol (e.g. methanol) byproduct of the reaction removed by an inert stripping or sparging agent, such as nitrogen, carbon dioxide, superheated steam, inert volatile organic compounds such as hexane, or noble gases such as argon. This inert gas stripping of the lower alkyl alcohol can be accomplished under vacuum, atmospheric, or superatmospheric pressure. In an even more preferred embodiment, the inert gas, following exit from the column reactor, is treated (e.g. by cooling) such that the lower alkyl alcohol is reduced in the inert gas stripping agent. The inert gas stripping agent with reduced lower alkyl alcohol levels can then be recycled back to the bottom (outlet) of the column reactor for reuse. Accordingly, there is at least some lower alkyl alcohol introduced at the outlet of the column reactor.

The total ester reactant to polyol esterifiable site in the final stages should be from about 0.9:1 to about 1.4:1, preferably from about 1:1 to about 1.2:1. The reduction or removal, of soap is preferred for column or film reactors to reduce the viscosity for improved operation.

In either a batch, semi-batch, or continuous process, the combination of (1) small particle size polyol, preferably obtained by mechanical size reduction to avoid the complications associated with solvent removal, (2) low levels of catalyst, preferably having a small particle size, (3) low levels of soap is highly desirable since such a combination provides a fast reaction while minimizing the amount of unwanted materials that are present and that must eventually be removed, (4) a residence time of about 1.0 to about 3 hours, more particularly from about 1.0 to about 2.2 hours in the second stage, and (5) the partial pressure of the lower alkyl alcohol (e.g. methanol) is maintained between about 0.0013 psia and about 0.26 psia, more preferably between about 0.013 psia and about 0.078 psia in a recycled inert gas stream. Maintaining a sufficient amount of lower alkyl alcohol in the recylced inert gas stream is useful for producing product that has a minimum amount of mono, di, tri, tetra, and penta esters. In particular, a sufficient amount of lower alkyl alcohol can be maintained in the recycled inert gas stream to provide a level of n–3 and lower esters of less than 0.5 percent by weight of the polyol polyesters in the final reaction product.

The combination of polyol removal with these improvements is desirable to improve both the speed of esterification and the degree of esterification completeness. Polyol that has not been dissolved in the early stage(s) of the reaction can interfere with the degree of completion.

Higher pressures such as atmospheric or superatmospheric pressure have the additional advantage of reducing air leakage into the reaction system. In a heated reaction system, air will react immediately with any fatty material. This will degrade the color, odor, flavor and physical properties of the fully esterified product. Reaction of air with fatty materials will also produce short chain and unsaturated soap, which will cause the reaction mixture to thicken appreciably in the second stage. This thickening will slow down the reaction by limiting the mass transfer of methanol or alcohol by-product out of the liquid phase. Thus, air leakage will detrimentally affect both the reaction rate and product quality.

Higher pressure, especially in the last stages of the reaction and more especially in the last stages of a continuous process is desirable since the combination makes it possible to fabricate the reaction apparatus without making provision for the maintenance of the more extreme conditions required by prior processes and allows for savings in energy usage in addition to the avoidance of the formation of undesirable and/or unneeded by-products. The savings are even greater in the preferred "plug-flow" final stages of the process where the conditions have to be maintained throughout the portion of the apparatus where the final stages of the reaction occur.

The combination of backmixing in the initial stage(s) and plug-flow conditions in the later stage(s) is highly preferred, especially for a continuous process, or mixed batch/continuous process, or continuous/batch process as it helps maintain optimum conditions for initiating the reaction between ingredients that are normally not compatible and then maximizing the final degree of esterification of the polyol.

The preferred products of the processes described herein have a combined detectable difatty alkyl ketone and beta-ketoester content that is less than about 350 ppm, preferably less than about 300 ppm. The preferred products contain less than about 4,000 ppm, preferably less than about 3,000 ppm of materials other than the desired polyol polyester. However, in products made by commercial processes of the types disclosed herein there is usually a detectable level, typically more than about 50 ppm of such other materials. The very low levels of by-products are achieved by the improvements herein, using good quality methyl esters as described herein before, and applying finished product clean-up procedures as described hereinafter. Maintaining difatty ketone and beta ketoester levels of less than about 350 ppm by weight is aided by the maintenance of a minimum level of lower alkyl alcohol in the recycled inert gas stream, as described above.

The Reaction

In general, by way of example, an initial heterogeneous reaction mixture comprises from about 10% to about 30%, preferably from about 14% to about 18%, by weight of polyol; from about 0.3 to about 1.4, preferably from about 0.3 to about 0.7 moles of fatty acid ester per esterifiable hydroxy groups on the polyol; an effective amount of lower partial polyol esters or from about 0.001 to about 0.6, preferably from about 0.05 to about 0.1, moles of alkali metal fatty acid soap per mole of the polyol; and from about 0.01 to about 0.5 mole per mole of the polyol of basic catalyst component. If desired, the reaction can be run in one or more reactors, although two reactors is preferable. In any later stage, additional fatty acid esters and, possibly, a more reactive catalyst can be added. After the initial stage, and before entering stage 2 any unreacted polyol is removed or decreased to a level of less than about 0.5% more preferably less than about 0.2%. In any second, or later step, additional fatty acid ester can be added to raise the overall ratio of fatty acyl groups to the esterifiable hydroxy sites on the polyol to from about 0.9:1 to about 1.4:1, preferably from about 1:1 to about 1.2:1. A preferred catalyst in the initial step is potassium carbonate, potassium methoxide, and/or residual base in the soap, as described herein before and, in any later step, the preferred catalysts are potassium and/or sodium carbonates and/or methoxides.

The reaction mixture is heated to a temperature within the range from about 130° C. to about 150° C., under vacuum with or without inert gas sparging or at or about atmospheric pressure with inert gas sparging. It is highly preferred that the reaction mixture, or mixtures, be stirred as vigorously as possible. The mixing is increased in the subsequent stages by the preferred step of sparging with an inert gas, preferably nitrogen, carbon dioxide, or low molecular weight hydrocarbons. With sparging, the removal of volatile alcohol produced in the reaction is promoted and the reaction rate is increased.

If even lower levels of n–3 and lower ester are desired with a fully esterified polyol level of 70–85 percent by weight, the following additional step can be used. Fresh reaction crude with a fully esterified polyol level of between about 70 and about 85 percent by weight and less than about 1.5 percent, and in one embodiment less than about 1.0 percent, by weight n–3 and lower esters can be held in a vessel (after the plug flow reaction stage) at a temperature of greater than about 90 degrees Centigrade, preferably between about 130 and 170 degrees Centigrade, for about 5 to about 600 minutes, more particularly about 30 to 300 minutes, and even more particularly between about 30 and about 120 minutes.

Finished Product Clean-up

After the reaction has reached the desired state of completion, the catalyst, the excess fatty esters, and the emulsifier, e.g., soap, must be removed if they cannot be used in the eventual consumption of the polyol fatty acid polyesters. The soap and catalyst can be removed to a large extent by a water separation step. However, it is an advantage of the processes herein that the level of catalyst, soap, and/or unreacted polyol and/or ester reactant present can be reduced drastically. Water is added, preferably at a ratio of from about 0.5:1 to about 10:1 relative to the amount of soap being removed. This low water level which is much less than would normally be considered desirable, surprisingly results in a better removal of the soap and catalyst than is achieved with more water, e.g., 20–40%. Separation of the soap and catalyst is facilitated by passing the water and reaction mixture through a centrifuge.

After centrifugation, the reaction mix can still contain an undesirable level of residual soap and/or color bodies. It is useful to repeat the water washing step followed by gravity or centrifugal separation of the aqueous phase. A subsequent vacuum drying and adsorptive bleaching operation can be used in combination with, or instead of, this second washing step. Drying and/or adsorptive bleaching operations, that use adsorbents such as bleaching earth and/or silica gel, are typical operations for processing edible oils. The adsorbents are added, preferably at a level of from about 0.1% to about 10% by weight of the dry reaction mix. After the bleaching operation is completed, the adsorbents are removed from the reaction mixture by filtration. The second stage water washing, and/or drying, and/or adsorptive bleaching completes the removal of soap and color bodies and prepares the reaction mixture for removal of any unreacted fatty acid ester.

A useful known process that can be used, in addition to the improvements described hereinafter, for removing unreacted materials, e.g., fatty acid ester reactant, and any other undesirable materials comprises a high temperature vacuum steam distillation process, and involves deaerating the polyol polyester to a level of less than about 0.10% by volume of dissolved oxygen and heating the deaerated oil to a temperature between about 390° F. (200° C.) and about 480° F. (250° C.) and then stripping with a stripping medium in the amount of about 0.2% to about 20% by weight of the oil at an absolute pressure of less than about 15 mm Hg for a time of between about 5 seconds and about 15 minutes. This vacuum stripping at very high temperatures for short residence times minimizes the content of undesirable materials. It is desirable to either maintain the temperature below about 450° F. (230° C.), preferably less than about 350° F. (about 180° C.), in a batch deodorizer, or admix the polyol polyester with a fatty acid triglyceride to protect the polyol polyester from excessive thermal degradation. Removal of such unreacted materials and other undesirable materials can also be desirably effected in a wiped film heat exchanger or other film evaporator.

Another useful improvement in finished product clean-up, involves adding a small amount of solubilised base (e.g., potassium hydroxide or potassium methoxide, solubilised in methanol) before distillation of any excess fatty acid ester reactant. The solubilised base improves the oxidative stability of the polyol fatty acid polyesters. The solvent for the base is preferably non-aqueous and the pH, measured at 120° F. (48.9° C.) on a 10% polyol fatty acid polyester solution in water/isopropanol, is from about 6.5 to about 9.

After the initial treatments, as described herein before, the undesirable materials can reform due to degradation of the oil/fatty acid ester. In addition, some undesirable color materials remain after the high temperature vacuum steam distillation process. The very low levels of color/odor/flavor materials, precursors, and/or oxidation products most preferred for use herein can be achieved by a clean-up procedure comprising one or more steps including, but not limited to:

(1) a step involving treatment with silica gel having the following properties: (a) a particle size of ranging from about 10 to about 30, preferably from about 20 to about 25 microns; (b) average pore diameter of from about 50 to about 70 microns; (c) surface area of from about 720 to about 800, preferably from about 770 to about 800 m$^2$/gm; (d) pore volume of from about 0.9 to about 1.9, preferably from about 1.2 to about 1.4 cm$^3$/gm; (e) a pH of from about 5 to about 8, preferably from about 5 to about 7.3 measured at a level of about 5% in water; and (f) total volatiles of less than about 20%, preferably from about 6.5% to about 10.5%, and more preferably from about 8% to about 10.5%. Such silica gels are extremely effective as compared to other known materials. Said silica gel is added to the product at levels of from about 0.25% to about 5%, preferably from about 1% to about 2%.

The use of the silica gel inevitably introduces oxygen, from entrapped air, into the polyester. It has been discovered, surprisingly, that oxygen can provide a benefit. Therefore, another process step involves introducing oxygen up to about saturation level, as a separate step and/or by the silica gel, and then raising the temperature to at least about 200° F. (about 90° C.), preferably at least about 380° F. (about 190° C.), but less than about 425° F. (about 220° C.), preferably less than about 400° F. (about 205° C.), to produce peroxygen groups and hold the product at the elevated temperature for a period of time sufficient to reduce the peroxygen content and/or reduce the content of colored materials present, e.g., from about 1 to about 150 minutes, preferably from about 1 to about 20 minutes, and most preferably from about 5 to about 10 minutes. (The level of oxygen in the polyol polyester is believed to be from about 0.001 to about 0.16 volumes of oxygen per volume of polyol polyester assuming similar values to those reported for triglycerides.) This can be accomplished separately, or in combination with a steam deodorization step, as described herein before. The time should not be so long as to start again increasing the color. When this oxygen/heat treatment step is used, it is possible to use a wider range of silica gels in place of the preferred silica gel of step (1) and achieve acceptable results. The best results, however, are achieved with the preferred silica gel. Any steam deodorization steps prior to the silica gel bleaching step and/or after the heat treatment step can be accomplished in the presence of a conventional triglyceride in ratios of higher polyol polyester to triglyceride of from about 1:10 to about 10:1, preferably from about 1:5 to about 5:1, more preferably from about 1:3 to about 3:1. This "codeodorization" minimizes thermal degradation of said polyester. The operating conditions for codeodorization are from about 300° F. (about 150° C.) to about 600° F. (about 315° C.), preferably from about 350–525° F. (about 175–275° C.); about 0.1–20 mm Hg (preferably about 1–10 mm Hg) vacuum; and steam to product ratio of about 0.001–0.30 (preferably 0.005–0.10). As compared to deodorization of the polyol polyester by itself, codeodorization permits the use of higher temperatures, e.g., from about 300° F. (150° C.) to about 600° F. (315° C.), preferably from about 350° F. (175° C.) to about 525° F. (275° C.), and/or longer times without excessive degradation and can be desirable if equipment limitations are present. The triglyceride is usefully any common triglyceride, e.g., those derived from cottonseed, peanut, safflower, sunflower, coconut, rapeseed, canola, palm, palm kernel, and/or soybean oils.

When the initial reactants have been properly cleaned up and the preceding cleanup steps have been applied properly, the color of the polyol polyester is less than about 3.0, preferably less than about 1.2, more preferably less than about 0.8 Lovibond Red, and the flavor grade of the polyol polyester is at least 7, preferably at least 8 panel score units (psu) as measured by a panel of experts using a grade system in which 10 is bland and 1 is severely oxidized. Such a finished polyol polyester has improved oxidative, flavor, and thermal stability during its subsequent uses. When combined with a typical triglyceride, containing natural antioxidants, in ratios of polyol polyester to triglyceride of from about 1:10 to about 10:1, preferably at ratios of from about 1:3 to about 3:1, more preferably at ratios of from about 1:3 to about 1:1, the stability is further surprisingly enhanced. Apparently, the reactive materials are reduced to a level where the natural antioxidants can provide improved long term stability.

Combinations of one or more of these cleanup steps reduce the quantity of undesired materials to a very low level, typically from about 50 ppm to about 4,000 ppm, most preferably less than about 3,000 ppm. For example, the products of the processes described herein can contain less than about 350 ppm, preferably less than about 300 ppm of di-fatty alkyl ketone and beta ketoester which are typically present in products prepared by (fatty acid ester)/polyol interesterification reactions. This is especially true when the methyl ester excess is low and/or lower temperatures are used.

Especially preferred polyol polyesters are those which have been esterified to a level of more than about 50%, preferably more than about 70%, and more preferably more than about 80% octaester for use in preparing liquid shortenings and from about 80% to about 85% octaester for "solid" shortenings. Such sucrose polyesters have superior thermal stability, especially when they contain only low levels of color/odor aterials and/or other oxidation products.

EXAMPLES

All percentages, parts and ratios herein are by weight unless otherwise specified.

Example 1

This example demonstrates one embodiment of the first stage of the reaction, i.e., the initial transesterification, which comprises reacting each polyol molecule, i.e. sucrose, with at least one fatty acid alkyl, i.e., methyl, ester molecule. The reactor system employed in this example comprises two stainless steel tank reactors in series, and each having an agitator, a liquid level control system, a heater, a recirculation pump, and temperature and pressure sensors. Sucrose, cottonseed fatty acid alkyl, i.e. methyl, esters, potassium stearate, and potassium carbonate are fed into the first reactor in the series at approximately the following molar ratios:

| Materials | Molar Ratio |
| --- | --- |
| Fatty acid methyl ester: sucrose | 5:1 |
| Potassium stearate (soap): sucrose | 0.2:1 |
| Potassium carbonate (catalyst): sucrose | 0.15:1 |

Both reactors are operated at about 275° F., and vacuum is applied to both reactors. Both reactors act as continuous stirred tank reactors (CSTR's), i.e., the reactors are designed to have backmixing. Backmixing is desirable in this stage of the reaction so that sucrose mono, di, and triester products of the reaction are maintained in intimate contact with incoming unreacted polyol. The sucrose mono-, di-, and triesters solubilize the solid sucrose into the reaction mixture, enabling it to react more readily with the fatty acid lower alkyl esters. The average residence time of the reaction mixture in the first reactor is about 3 hours. The reaction mixture is pumped from the first reactor to the second reactor at the same rate as the in-going feed material to the first reactor so that the content in the first reactor is maintained constant. The reaction material pumped into the second reactor has an average residence time of about 1 hours therein. Reaction material is pumped out of the second reactor at the same rate as the in-going feed to the second reactor to maintain the content in the second reactor constant. The reaction material from the second reactor is then transferred to a multistage column reactor operating at about 26 psia (bottom of column). The product from the second reactor has a degree of esterification of the sucrose of about 63% with an unreacted sucrose level of about 0.5 weight %.

Example 2

The first step reaction product from Example 1 is pumped continuously into a multistage column reactor, together with a second portion of fatty acid methyl esters in an amount providing a total fatty acid methyl ester:sucrose molar ratio of about 11:1. Additional potassium carbonate is added to the incoming reaction material to provide a total potassium carbonate:sucrose molar ratio of about 0.15:1. The column is designed to approximate plug flow, and to provide intimate contact between the stripping gas and the reaction liquid.

Five plates are placed in the column at equal intervals to segment the column into 5 sections. Each plate has several small holes that allow the nitrogen gas to pass upwardly through the plate and downcomer tubes that allow the liquid to flow from one segment to another. Nitrogen is introduced at the bottom of the column and travels upward through the column. In each segment, the nitrogen is dispersed into the liquid by radial shear agitation provided by the agitators to produce very small bubbles. The nitrogen strips the methanol by-product from the reaction mixture, and proceeds upward through the column propelled by buoyant forces, from section to section. The nitrogen is exhausted from the column when it reaches the top. The nitrogen is then passed through a chilling apparatus, where the majority of the methanol is condensed from the nitrogen stream. The nitrogen is then recycled to the bottom of the column to be used again. The concentration of methanol in the nitrogen gas in the bottom section of the column is about 200 ppm. The reaction product is pumped from the bottom of the column. The reaction is operated at about 275° F. The reactor pressure at the top of the column is slightly above atmospheric. The weight ratio of nitrogen to the incoming liquid feed is about 1.5:1, and the average residence time of the liquid in the column is about 1.4 hours.

The reaction product from the bottom of the column contains about 77% sucrose octaester and about 0.5% sucrose pentaester.

Example 3

The reactions in this example are run in a manner similar to Example 2, except for the differing process parameters shown in the table below.

| Reaction | Residual unreacted sucrose going into the second stage reaction | Second stage residence time | Methanol level in the recirculated nitrogen into the second stage reaction | Sucrose octaester | Sucrose penta and lower esters |
|---|---|---|---|---|---|
| A | 0.2% | 1.4 hours | 200 ppm | 77% | 0.5% |
| B | 0.2% | 2 hours | 200 ppm | 78% | 0.4% |

This example demonstrates that increasing the residence time the second stage reaction can reduce sucrose penta and lower esters while maintaining the sucrose octa ester level between about 70 and about 85%.

Example 4

The reactions in this example are run in a manner similar to Example 2, except for the differing process parameters shown in the table below.

| Reaction | Residual unreacted sucrose going into the second stage reaction | Second stage residence time | Methanol level in the recirculated nitrogen into the second stage reaction | Sucrose octaester | Sucrose penta and lower esters |
|---|---|---|---|---|---|
| C | 0.3% | 1.6 hours | 700 ppm | 78% | 0.7% |
| D | 0.3% | 1.6 hours | 3000 ppm | 75% | 0.5% |

This example demonstrates that increasing the level of methanol in the recirculated nitrogen to the second stage reaction can reduce sucrose penta and lower esters while maintaining the sucrose octa ester level between about 70 and about 85%.

Example 5

The reactions in this example are run in a manner similar to Example 2, except for the differing process parameters shown in the table below.

| Reaction | Residual unreacted sucrose going into the second stage reaction | Second stage residence time | Methanol level in the recirculated nitrogen into the second stage reaction | Sucrose octaester | Sucrose penta and lower esters |
|---|---|---|---|---|---|
| E | 0.4% | 1.6 hours | 3000 ppm | 74% | 0.7% |
| F | 0.2% | 1.6 hours | 3000 ppm | 74% | 0.5% |

This example demonstrates that reducing the level of unreacted sucrose going into the second stage reaction can reduce sucrose penta and lower esters while maintaining the sucrose octa ester level between about 70 and about 85%.

Example 6

The reactions in this example are run in a manner similar to Example 2, except for the differing process parameters shown in the table below.

| Reaction | Residual unreacted sucrose going into the second stage reaction | Second stage residence time | Methanol level in the recirculated nitrogen into the second stage reaction | Heating time for the second stage reaction product after the reaction | Sucrose octaester | Sucrose penta and lower esters |
|---|---|---|---|---|---|---|
| G | 0.3% | 1.6 hours | 1500 ppm | 0 minutes | 78% | 0.7% |
| H | 0.3% | 1.6 hours | 1500 ppm | 45 minutes | 78% | 0.4% |

This example demonstrates heating the second stage reaction product after the reaction can reduce sucrose penta and lower esters while maintaining the sucrose octa ester level between about 70 and about 85%.

Example 7

Reaction product from the bottom of the column is prepared in a way similar to Example 2. The composition of this product is about 78.3% octacester and about 0.37% pentaester.

About 200 g of this unrefined polyol polyester is added to a one liter round bottom 3-neck flask, fitted with a 2 inch (5 cm) long "half moon" impeller is used for the reactor. A nitrogen bubbler is attached to one of the inlets to maintain a static nitrogen blanket in the headspace of the reactor. The flask is agitated at about 150 rpm. The temperature is raised to about 275° F. while maintaining agitation and the nitrogen blanket and the reaction mixture is allowed to equilibrate for about 2 hours. No sparging of the reaction mix is done. The pentaester and octaester results appear in Table I.

TABLE 1

| Time, Hours | % Octaester | % Pentaester |
|---|---|---|
| 0 | 78.3 | 0.37 |
| 0.5 | 76.9 | 0.24 |
| 1.0 | 76.8 | 0.23 |
| 1.5 | 76.7 | 0.18 |
| 2.0 | 76.2 | 0.20 |

What is claimed:

1. A continuous, solvent free process for preparing polyol fatty acid polyesters by interesterifying polyol containing n esterifiable hydroxy groups and fatty acid ester, wherein n is more than about four, and wherein the process comprises:

a first stage reaction providing a first stage reaction product having a level of unreacted polyol of less than about 0.50 percent, and wherein the degree of esterification of the reacted polyol in the first stage reaction product is between about 15 percent and about 75 percent;

a second stage reaction, the second stage reaction receiving the first stage reaction product and providing further esterification of the first stage reaction product to provide a second stage reaction product, wherein the second stage reaction is controlled to maintain a degree of esterification of the polyol such that no more than about 85 percent by weight of the esterified polyol molecules in the second stage reaction product are fully esterified, and wherein the second stage reaction is controlled to reduce the level of n -y and lower polyol esters to less than about 1.0 percent by weight of the esterified polyol molecules, wherein n -y and lower polyol esters are at least partially digestible within the human gastrointestinal tract.

2. The process of claim 1 wherein the second stage reaction is controlled to reduce the level of n–3 and lower polyol esters to less than about 1.0 percent by weight of the esterified polyol molecules, while maintaining between about 70 percent and about 85 percent by weight of the esterified polyol molecules fully esterified.

3. The process of claim 2 wherein the second stage reaction is controlled to reduce the level of n–3 and lower polyol esters to less than about 0.50 percent by weight of the esterified polyol molecules, while maintaining between about 70 percent and about 85 percent by weight of the esterified polyol molecules fully esterified.

4. The process of claim 2 wherein the second stage reaction is controlled to reduce the level of n–3 and lower polyol esters to less than about 0.50 percent by weight of the esterified polyol molecules while reducing the level of fully esterified polyol molecules.

5. The process of claim 2 wherein the second stage reaction is controlled by reducing the level of unreacted polyol in the first stage reaction product to less than about 0.20 percent.

6. The process of claim 2 wherein the level of n–3 and lower esters is maintained by controlling the residence time of the polyol esters in the second stage reaction to be between 1 hour and 6 hours.

7. The process of claim 2 wherein the step of controlling the second stage reaction comprises controlling the level of lower alkyl C1–C4 alcohol in the second stage reaction.

8. The process of claim 7 wherein the step of controlling the level of lower alkyl C1–C4 alcohol in the second stage reaction comprises providing a sufficient level of lower alkyl C1–C4 alcohol to maintain between about 70 percent and about 85 percent by weight of the esterified polyol molecules fully esterified while reducing the level of n–3 and lower esters.

9. The process of claim 8 wherein the step of providing a sufficient level of lower alkyl C1–C4 alcohol comprises adding methanol to the second stage reaction.

10. The process of claim 9 comprising providing an inert gas sparge to the second stage reaction, wherein the inert gas sparge contains methanol.

11. The process of claim 10 wherein the step of providing an inert gas sparge comprises providing a recycled inert gas sparge containing methanol.

12. The process of claim 11 wherein the step of providing a recycled inert gas sparge comprises providing a recycled inert gas sparge containing between about 0.0013 and about 0.26 psia methanol partial pressure.

13. The process of claim 1 further comprising the step of heating the reaction product of the second stage after the completion of the second stage reaction, wherein the step of heating the reaction product of the second stage is performed without removing lower alkyl alcohol byproduct and wherein the step of heating the reaction product of the second stage is performed with an effective amount of catalyst, the step of heating reaction product of the second stage reducing the level of n–3 and lower esters to less than about 1 percent by weight of the polyol molecules, while maintaining the level of esterification of the polyol such that between about 70 percent and about 85 percent by weight of the esterified polyol molecules are fully esterified.

14. The process of claim 13 wherein the step of heating the reaction product of the second stage comprises heating the reaction product at a temperature of at least 90 degrees Centigrade for at least 5 minutes.

15. The process of claim 14 wherein the step of heating the reaction product comprises heating the reaction product at a temperature of between about 130 and about 170 degrees centigrade for between about 30 and about 120 minutes.

16. The process of claim 1 wherein n is at least 6.

17. The process of claim 2 wherein n is at least 6.

18. The process of claim 17 wherein n is at least 8.

19. A process for preparing sucrose fatty acid polyester, the process comprising:

providing a reaction product of sucrose fatty acid polyester comprising between about 70 and about 85 percent by weight sucrose octaester and no more than about 1.0 percent by weight penta and lower sucrose ester; and reducing the level of penta and lower sucrose ester to less than about 0.6 percent while maintaining the level of sucrose octaester between about 70 and about 85 percent.

20. The process of claim 19 wherein the step of reducing the level of penta and lower sucrose ester comprises reducing the level of penta and lower sucrose ester without increasing the level of sucrose octaester.

21. The process of claim 20 wherein the step of reducing the level of penta and lower sucrose ester comprises reducing the level of penta and lower sucrose ester while decreasing the level of sucrose octaester.

22. The process of claim 19 comprising reducing the level of penta and lower sucrose ester to less than about 0.5 percent while maintaining the level of sucrose octaester between about 70 and about 85 percent.

23. The process of claim 22 comprising reducing the level of penta and lower sucrose ester to less than about 0.20 percent while maintaining the level of sucrose octaester between about 70 and about 85 percent.

24. The process of claim 19 comprising the step of reducing the level of unreacted sucrose to less than about 0.30 percent to promote the reduction of the level of penta and lower sucrose ester.

25. The process of claim 19 comprising the step of controlling a reaction residence time to promote the reduction of the level of penta and lower sucrose ester.

26. The process of claim 19 comprising controlling the level of C1–C4 alcohol in a reaction stage to promote the reduction of the level of penta and lower sucrose ester.

27. The process of claim 19 comprising heating the reaction product to promote the reduction of the level of penta and lower sucrose ester.

28. The process of claim 27 wherein the step of heating the reaction product comprises heating the reaction product at a temperature greater than about 90 degrees Centigrade for between about 5 and about 600 minutes.

29. The process of claim 27 wherein the step of heating the reaction product comprises heating the reaction product at a pressure selected so as not to substantially increase the level of sucrose octaester.

30. The process of claim 27 where the step of heating the reaction product comprises heating the reaction product at a pressure greater than or equal to atmospheric pressure.

* * * * *